United States Patent
Nita et al.

[11] Patent Number: 5,957,882
[45] Date of Patent: Sep. 28, 1999

[54] ULTRASOUND DEVICES FOR ABLATING AND REMOVING OBSTRUCTIVE MATTER FROM ANATOMICAL PASSAGEWAYS AND BLOOD VESSELS

[75] Inventors: Henry Nita, Mission Viejo; Timothy C. Mills, Corona Del Mar, both of Calif.

[73] Assignee: Advanced Cardiovascular Systems, Inc., Santa Clara, Calif.

[21] Appl. No.: 08/815,673

[22] Filed: Mar. 12, 1997

Related U.S. Application Data

[63] Continuation of application No. 08/222,999, Apr. 5, 1994, abandoned, which is a continuation-in-part of application No. 07/640,190, Jan. 11, 1991, Pat. No. 5,304,115.

[51] Int. Cl.$^6$ .................................................. A61B 17/20
[52] U.S. Cl. ................................ 604/22; 601/2; 606/169
[58] Field of Search ........................ 604/21, 22; 606/159, 606/169–171; 601/2

[56] References Cited

U.S. PATENT DOCUMENTS

| | | |
|---|---|---|
| 3,809,093 | 5/1974 | Abraham . |
| 3,823,717 | 7/1974 | Pohlman . |
| 4,223,676 | 9/1980 | Wuchinich et al. . |
| 4,337,090 | 6/1982 | Harrison . |
| 4,431,006 | 2/1984 | Trimmer et al. . |
| 4,474,180 | 10/1984 | Angulo . |
| 4,505,767 | 3/1985 | Quin . |
| 4,565,589 | 1/1986 | Harrison . |
| 4,587,958 | 5/1986 | Noguchi et al. . |
| 4,587,972 | 5/1986 | Morantte . |
| 4,589,419 | 5/1986 | Laughlin et al. . |
| 4,665,906 | 5/1987 | Jervis . |
| 4,692,139 | 9/1987 | Stiles . |
| 4,741,731 | 5/1988 | Starck . |
| 4,748,971 | 6/1988 | Borodulin et al. . |
| 4,750,902 | 6/1988 | Wuchinich et al. . |
| 4,764,165 | 8/1988 | Reimels . |
| 4,794,931 | 1/1989 | Yock . |
| 4,799,496 | 1/1989 | Hargraves . |
| 4,800,876 | 1/1989 | Fox et al. . |

(List continued on next page.)

FOREIGN PATENT DOCUMENTS

| | | |
|---|---|---|
| 293472 | 11/1986 | European Pat. Off. . |
| 0 208 175 | 1/1987 | European Pat. Off. . |
| 0 316 976 | 5/1989 | European Pat. Off. . |
| 315290 | 10/1989 | European Pat. Off. . |
| 443256 | 12/1990 | European Pat. Off. . |
| 472368 | 2/1992 | European Pat. Off. . |
| 2 641 693 | of 0000 | France . |
| 2 643 272 | of 0000 | France . |
| 2453058 | 5/1976 | Germany . |
| 2541919 | 3/1977 | Germany . |
| 2703486 | 12/1977 | Germany . |
| 3707921A1 | 3/1986 | Germany . |
| 3726210 | 8/1987 | Germany . |
| 1520448 | 6/1987 | United Kingdom . |
| 2208138 | 3/1989 | United Kingdom . |
| 2212267 | 7/1989 | United Kingdom . |
| WO 87/01276 | 3/1987 | WIPO . |
| WO 87/05793 | 10/1987 | WIPO . |
| WO 89/05123 | 6/1989 | WIPO . |
| WO 89/06515 | 7/1989 | WIPO . |
| WO 89/07419 | 8/1989 | WIPO . |
| WO 90/01300 | 2/1990 | WIPO . |
| WO 90/07303 | 7/1990 | WIPO . |
| WO 91/02489 | 3/1991 | WIPO . |
| WO 91/14401 | 10/1991 | WIPO . |
| WO 92/10140 | 6/1992 | WIPO . |
| WO 92/11815 | 7/1992 | WIPO . |
| WO 92/15253 | 9/1992 | WIPO . |

*Primary Examiner*—Corrine McDermott
*Attorney, Agent, or Firm*—Fulwider Patton Lee & Utecht, LLP

[57] ABSTRACT

An ultrasonic catheter device for removing obstructive matter from anatomical passageway includes a tubular body with distal head member in which a plurality of fluid passageways are formed about the lateral surface to expel fluid outward generally perpendicular to the longitudinal axis of the body.

2 Claims, 3 Drawing Sheets

U.S. PATENT DOCUMENTS

| | | |
|---|---|---|
| 4,808,153 | 2/1989 | Parisi . |
| 4,811,743 | 3/1989 | Stevens . |
| 4,821,731 | 4/1989 | Martinelli . |
| 4,841,977 | 6/1989 | Griffith . |
| 4,844,092 | 7/1989 | Rydell . |
| 4,867,141 | 9/1989 | Nakada . |
| 4,870,953 | 10/1989 | DonMichael . |
| 4,898,575 | 2/1990 | Fischell et al. . |
| 4,917,097 | 4/1990 | Proudian et al. . |
| 4,919,133 | 4/1990 | Chiang . |
| 4,920,954 | 5/1990 | Alliger et al. . |
| 4,924,863 | 5/1990 | Sterzer . |
| 4,936,281 | 6/1990 | Stasz . |
| 4,957,111 | 9/1990 | Millar . |
| 4,960,411 | 10/1990 | Buchbinder . |
| 4,966,583 | 10/1990 | Debbas . |
| 4,967,653 | 11/1990 | Hinz . |
| 4,967,753 | 11/1990 | Haase et al. . |
| 4,979,939 | 12/1990 | Shiber . |
| 4,988,356 | 1/1991 | Crittenden . |
| 4,989,583 | 2/1991 | Hood . |
| 5,058,570 | 10/1991 | Idemoto et al. . |
| 5,061,238 | 10/1991 | Shuler . |
| 5,069,664 | 12/1991 | Guess et al. . |
| 5,076,276 | 12/1991 | Sakurai et al. . |
| 5,100,423 | 3/1992 | Fearnot . |
| 5,151,085 | 9/1992 | Sakurai . |
| 5,163,421 | 11/1992 | Bernstein . |
| 5,188,589 | 2/1993 | Wypych . |
| 5,199,943 | 4/1993 | Wypych . |
| 5,211,625 | 5/1993 | Sakurai . |
| 5,242,385 | 9/1993 | Strukel . |
| 5,248,296 | 9/1993 | Alliger . |
| 5,255,669 | 10/1993 | Kubota . |
| 5,261,877 | 11/1993 | Fine . |
| 5,267,954 | 12/1993 | Nita ............ 604/22 |
| 5,269,297 | 12/1993 | Weng . |
| 5,312,328 | 5/1994 | Nita . |
| 5,342,292 | 8/1994 | Nita et al. ............ 604/22 |
| 5,368,558 | 11/1994 | Nita ............ 604/22 |
| 5,380,274 | 1/1995 | Nita ............ 604/22 |

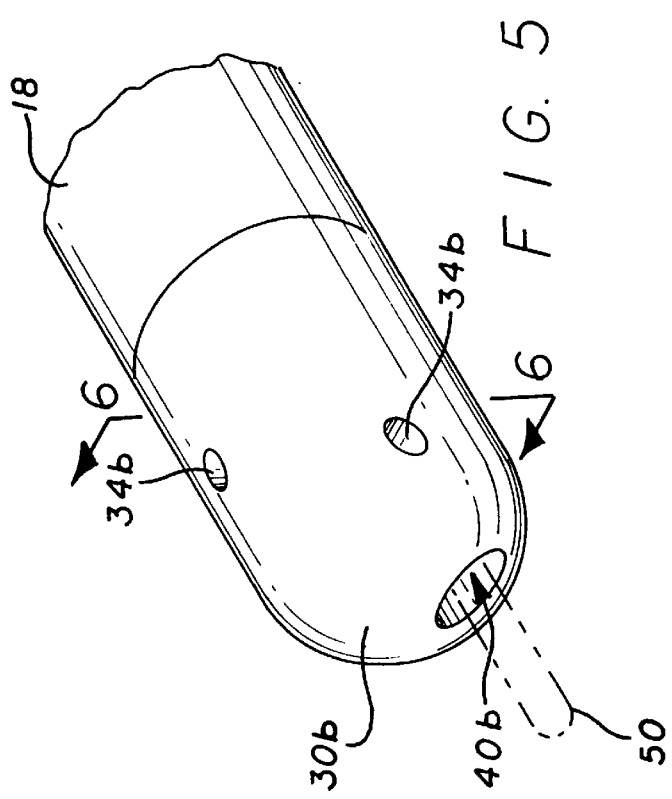
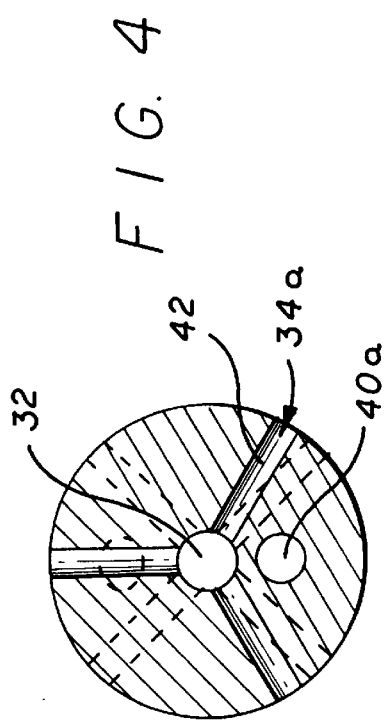
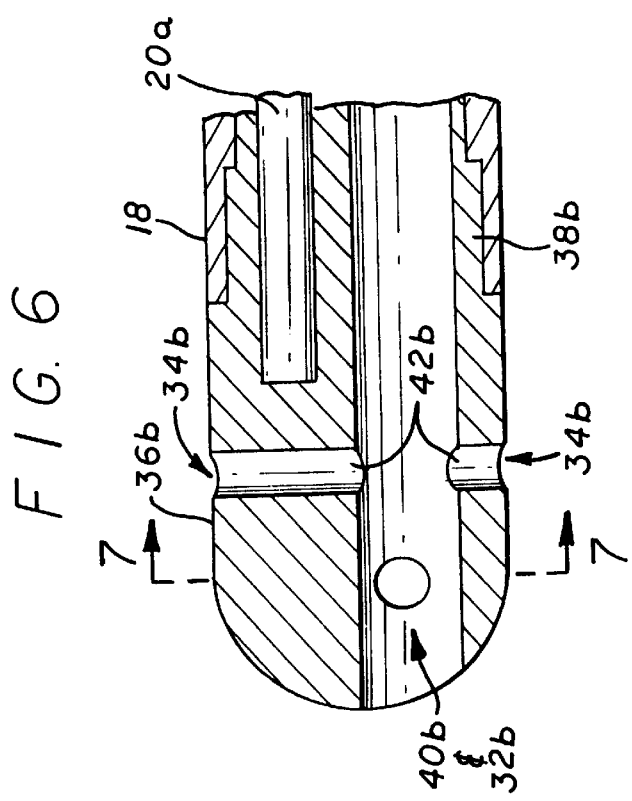

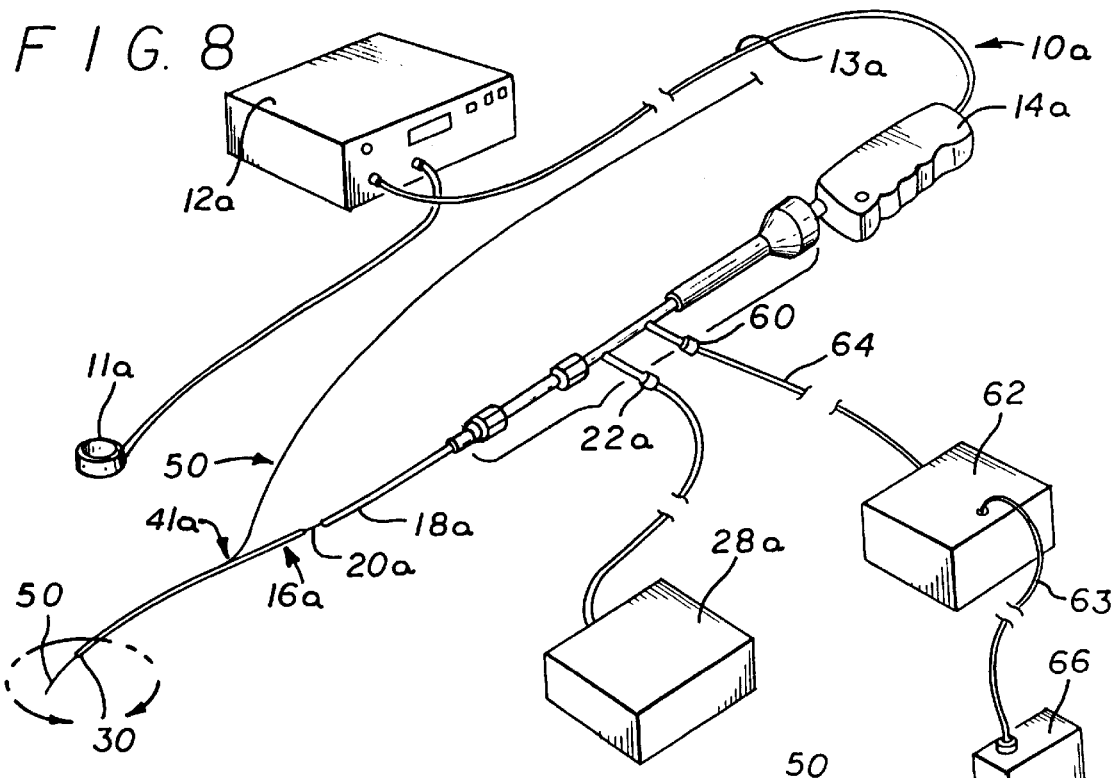
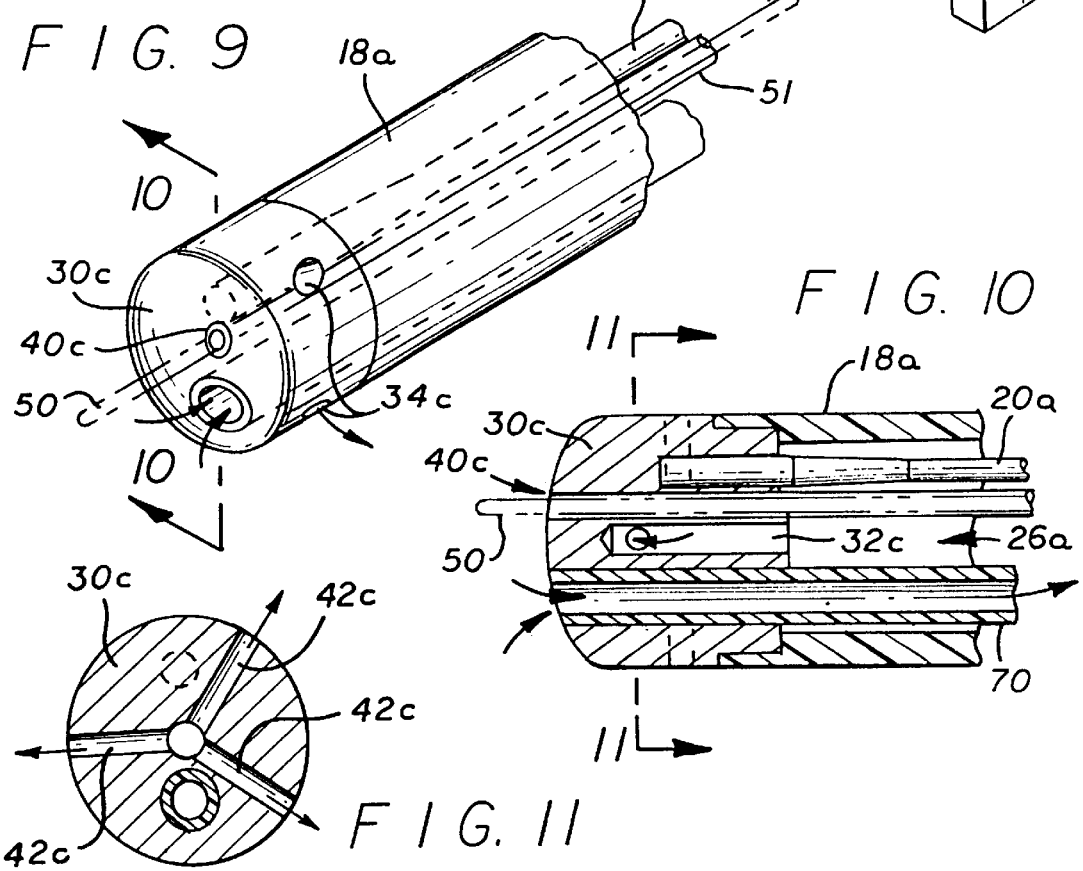

ULTRASOUND DEVICES FOR ABLATING AND REMOVING OBSTRUCTIVE MATTER FROM ANATOMICAL PASSAGEWAYS AND BLOOD VESSELS

RELATED APPLICATION AND INCORPORATION BY REFERENCE

This application is a continuation of application Ser. No. 08/222,999 filed Apr. 5, 1994, now abandoned, which is a continuation-in-part of U.S. patent application Ser. No. 07/640,190 filed Jan. 11, 1991 entitled ULTRASONIC ANGIOPLASTY DEVICE INCORPORATING IMPROVED TRANSMISSION MEMBER AND ABLATION PROBE, now U.S. Pat. No. 5,304,115, the entirety of which is expressly incorporated herein by reference.

Also, applicant expressly incorporates herein by reference the entirety of U.S. Pat. No. 5,267,954 entitled ULTRASOUND CATHETER FOR REMOVING OBSTRUCTIONS FROM TUBULAR ANATOMICAL STRUCTURES SUCH AS BLOOD VESSELS, issued Dec. 7, 1993.

FIELD OF THE INVENTION

The present invention pertains generally to medical equipment and, more particularly, to ultrasonic devices and methods for removing obstructive matter from anatomical passageways, including the removal of obstructive matter from the cerebral vasculature, prostate tissue from the urinary tract and/or obstructive matter from the fallopian tubes.

BACKGROUND OF THE INVENTION

The prior art has included various ultrasonically vibrated surgical and ablative instruments for treating obstructive disorders of blood vessels and other anatomical passageways or cavities.

The prior art devices which purportedly utilize ultrasonic energy, alone or in conjunction with other treatment modalities, to treat obstructions within blood vessels or other anatomical structures of the body include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al.), 4,920,954 (Alliger, et al.), and 5,100,423 (Fearnot), 4,136,700 (Broadwin), 4,192,294 (Vasilevsky), 4,750,448 (Wuchinich), 4,750,902 (Wuchinich), 4,765,332 (Fischell), 4,808,153 (Parisi), 4,832,023 (Murphy-Chutorian), 4,867,141 (Nakada), 4,870,953 (Don Michael), 4,877,033 (Seitz), 4,886,061 (Fischell), 4,922,902 (Wuchinich), 4,936,281 (Stasz), 4,974,581 (Wiksell) 4,989,588 (Kubota), 5,058,570 (Idemoto), 5,069,664 (Guess), 5,149,319 (Unger), 5,151,084 (Khek), 5,154,723 (Kubota), 5,156,143 (Bocquett), 5,163,421 (Bernstein), 5,163,433 (Kagawa), as well as foreign publications nos. W087-05739 (Cooper) W089-06515 (Bernstein, et al.), W090-0130 (Sonic Needle Corp.), EP316789 (Don Michael, et al), DE3,821,836 (Schubert), DE2,438,648 (Pohlman), GB 1,531,659 (Gekhman, et al.), EP 342448 (Bakelite), EP 293472 (Bakelite), and EP 209468 (Sarl).

Although the prior art has included numerous devices for ultrasonic treatment of intracorporeal obstructions, there remains a need in the art for the development of new and improved ultrasonic devices having improved or differing capabilities for specific blood vessels or regions of the body, such as the intracranial and extracranial vessels of the cerebral vasculature and/or the tubes and ducts of the genitourinary tracts of the male and female.

SUMMARY OF THE INVENTION

The present invention provides methods for ultrasonically treating obstructions of anatomical passageways of the mammalian body with concomitant infusion of a fluid (e.g., saline solution) in a manner which will dilate or fluidically expand the surrounding anatomical structure so as to facilitate passage of a catheter through the obstructed region of the anatomical structure. Methodologies in accordance with this embodiment of the invention are particularly useful in treating intravascular obstructions as well as obstructions of the male or female urogenital tract, including, but not limited to obstructions of the fallopian tubes and prostatic obstructions of the male urethra.

Further in accordance with the invention, there are provided methods for ultrasonically treating obstructions within anatomical passageways of the mammalian body while concomitantly aspirating and removing matter from the anatomical passageway so as to prevent escape of solid particles or other matter created or released by the ultrasonic treatment process. In accordance with this embodiment of the invention, there are provided methodologies which are particularly applicable in the ultrasonic treatment of obstructions within intracranial and extracranial cerebral blood vessels which supply blood to the mammalian brain.

Further in accordance with the invention, there is provided a first embodiment of an ultrasound treatment system incorporating an ultrasound delivery catheter having one or more fluid infusion lumens for infusing fluid through the catheter, to effect fluidic dilation of the anatomical structure wherein the obstruction is located.

Still further in accordance with the invention, there is provided a second embodiment of an ultrasound treatment system incorporating an ultrasound delivery catheter having at least one aspiration lumen extending longitudinally through the catheter to aspirate and remove particles or other debris from the anatomical structure wherein the obstruction is located.

Further objects and advantages of the invention will become apparent to those skilled in the art upon reading and understanding the following detailed description and the accompanying drawings.

BRIEF DESCRIPTION OF THE DRAWINGS

FIG. 4 is a cross-sectional view through line 4—4 of FIG. 3.

FIG. 5 is an enlarged perspective view of a second embodiment of a catheter tip which may be incorporated into the ultrasound system of FIG. 1.

FIG. 6 is a longitudinal sectional view through line 6—6 of FIG. 5.

FIG. 7 is a cross-sectional view through line 7—7 of FIG. 6.

FIG. 8 is a perspective view of an alternative configuration of an ultrasound treatment system of the present invention.

FIG. 9 is an enlarged perspective view of a distal catheter tip which may be incorporated into the ultrasound system of FIG. 8.

FIG. 10 is a longitudinal sectional view through line 10—10 of FIG. 9.

FIG. 11 is a cross-sectional view through line 11—11 of FIG. 10.

DETAILED DESCRIPTION OF THE PREFERRED EMBODIMENTS

The following detailed description and the accompanying are provided for purposes of describing and illustrating presently preferred embodiments of the invention and are not intended to cover every possible embodiment or configuration of the invention, nor are they intended to limit the scope of the accompanying claims in any way.

With references to the drawings, FIGS. 1–7 are directed to a first embodiment of the invention preferably useable to dilate and treat obstructive disorders of various anatomical passageways, including the urethra and/or fallopian tubes. FIGS. 8–11 are directed to a second embodiment of the invention preferably useable to effect a) ultrasonic ablation of obstructive matter and b) aspiration of the reduced or morseled matter from the treatment site, such as a cerebral blood vessel or other passageway of the body wherein prompt aspiration or removal of any solid matter is desired.

i. Elements and Components of the First Embodiment

Figure 1:
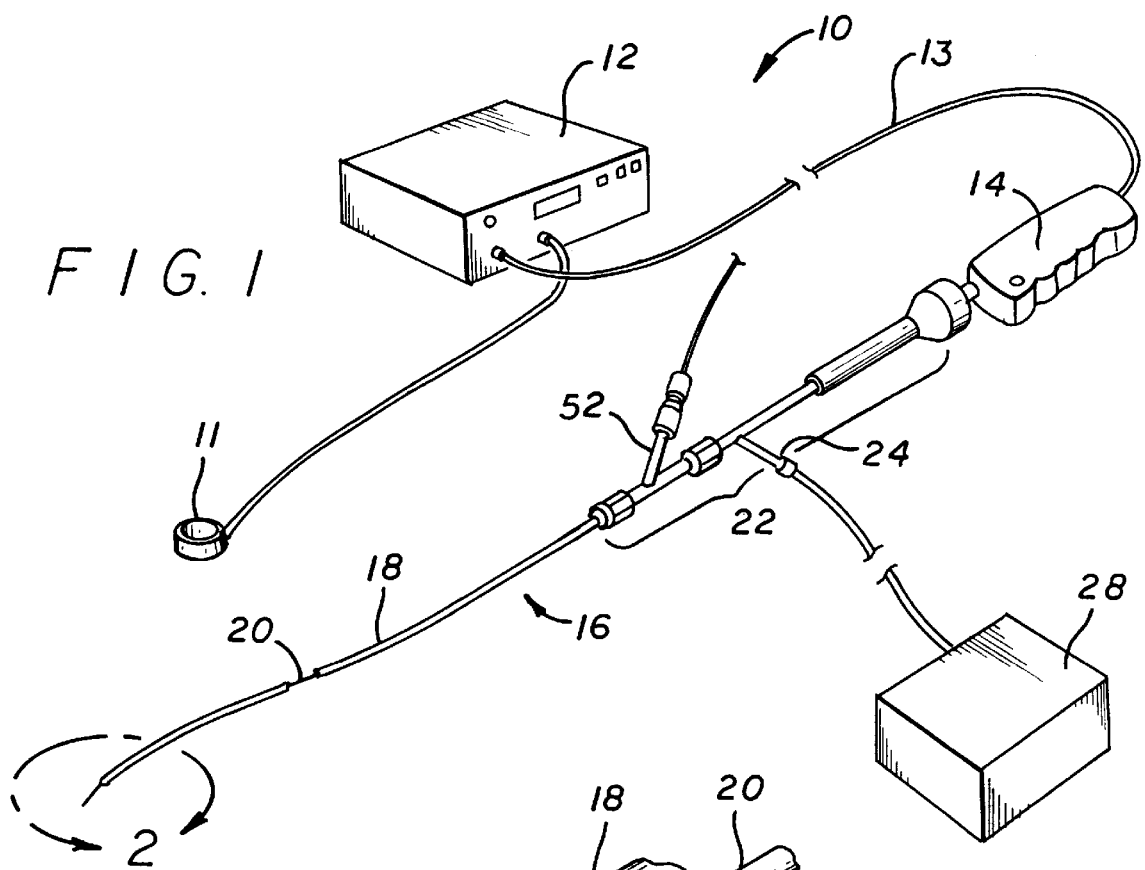
FIG. 1 is a perspective view of a first embodiment of an ultrasonic system of the present invention for removing obstructions from genitourinary pathways or other anatomical structures of the body.

A first embodiment of an ultrasound treatment system 10 of the present invention, shown in FIG. 1, comprises an electrical signal generator 12 (e.g., Model UAG-1110, Baxter Healthcare Corporation, Cardiovascular Group, Interventional Cardiology Division, Irvine, Calif.) connected by way of cable 13 to an ultrasound transducer 14 (e.g., Model UAT-1000, Baxter Healthcare Corporation, Irvine, Calif.) operable to convert the electrical signal from the signal generator 12, into ultrasonic vibration. An elongate ultrasound catheter 16 is coupled to the ultrasound transducer 14 to transmit ultrasonic vibration from the transducer 14 to a desired treatment location adjacent the distal end of the catheter 16.

The catheter 16 component of the first embodiment of the ultrasound treatment system 10 may comprise an elongate flexible catheter body 18 formed of pliable material and an elongate ultrasound transmission wire or member 20 which extends longitudinally through the catheter body 18. The ultrasound transmission wire or member 20 extends proximally through a proximal connector assembly 22 whereby the proximal end of the ultrasound transmission member 20 may be coupled or attached to the ultrasound generating horn of the ultrasound transducer 14. The distal end of the ultrasound transmission member 20 is coupled or attached to a distal head member 30 at the distal end of the catheter 16.

The structure and configuration of the proximal connector assembly 22 of the first embodiment may be the same as that described and shown in FIG. 10 of U.S. Pat. No. 5,267,954 (Nita), the entirety of such patent being hereby expressly incorporated herein by reference.

A fluid infusion sidearm 24 extends from proximal connector assembly 22 and is fluidly communicative with a hollow bore extending through at least a distal portion of the proximal connector assembly 22 and into an elongate hollow infusion fluid lumen 26 extending through the catheter body 18. A source 28 of pressurized or pumped liquid (e.g., 0.9% NaCl solution) is connected to the fluid infusion sidearm 24 to permit infusion of fluid through the bore of the proximal connector assembly 22 and through the elongate lumen 26 of the catheter body 18. A distal head member 30, is mounted on the distal end of the catheter body 18. Such distal head member may be of any suitable configuration, including the blunt horizontal faced configuration 30a shown in FIGS. 2–3 and the bullet-like configuration 30b shown in FIGS. 5–6. In any case, the distal head member 30 will be provided with one or more fluid outflow apertures 34 which are fluidly communicative with the fluid lumen 26 of the catheter body 18 to permit irrigation fluid to flow out of the distal head 30 of the catheter 16.

Figure 2:
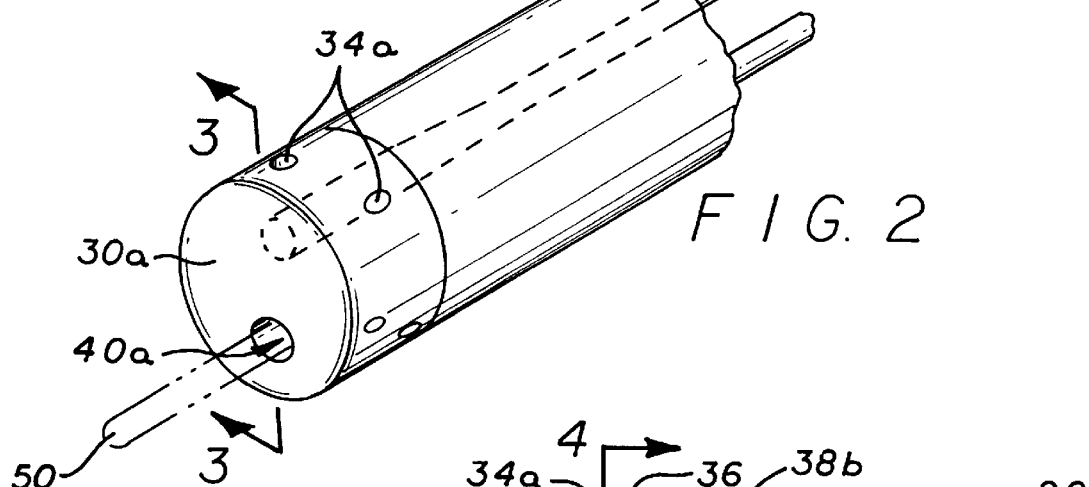
FIG. 2 is an enlarged perspective view of a first embodiment of a distal catheter tip which may be incorporated in the system of FIG. 1.
Figure 3:
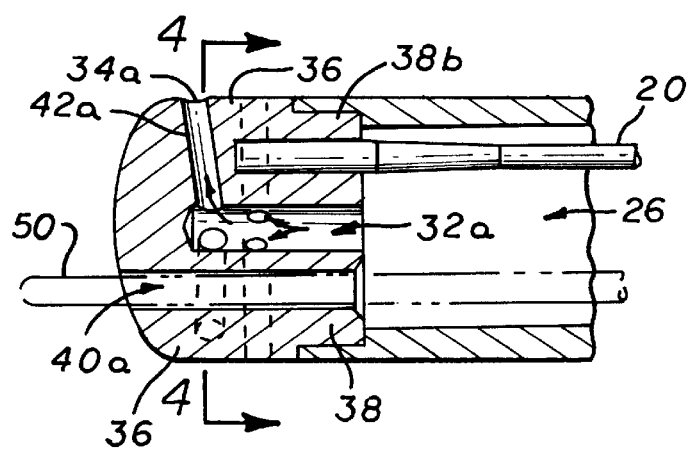
FIG. 3 is a longitudinal sectional view through line 3—3 of FIG. 2.

In the blunt distal head embodiment 30 shown in FIGS. 2–3, the configuration of the distal head member 30 is such that there is provided a frontal portion 36 having an outer diameter substantially equal to the outer diameter of the catheter body 18, and a rear portion 38 having an outer diameter substantially equal to the inner diameter at the distal head of the catheter lumen 26 by such configuration, the rear portion 38 of the distal head member 30 may be inserted into the distal end opening of the lumen 26 of catheter body 18 and secured thereto by frictional engagement, mechanical engagement, adhesive, heat sealing or other suitable means. The outer surface of the frontal portion 36 of the distal head member 30a is thus rendered substantially continuous and in smooth transition with the outer surface of the adjacent catheter body 18. The distal head member 30a has a central fluid passageway 32 formed therein, separate and apart from the guidewire passageway 40 which extends longitudinally through the lower portion of the distal head member 30. Such central fluid passageway 32 opens into ancillary passageways 42, said ancillary passageways 42 terminating laterally in the multiple fluid outflow apertures 34 formed in the sides of the distal head member 30. By such arrangement, fluid infused through the lumen 26 of the catheter body 18 will enter the central fluid passageway 32 of the distal head member 30 and will subsequently pass outwardly through the lateral fluid passageways 42 and out of the fluid outflow apertures 34. This may be accomplished while a guidewire (phantom lines) remains inserted into guidewire passageway 40, thereby substantially blocking fluid outflow through guidewire passageway 40.

The rate of fluid outflow through outflow apertures 34 may be controlled to effect any desired degree of irrigation and/or fluidic dilation of a surrounding anatomical structure (e.g., fallopian tube, ureter, duct, blood vessel, etc. . . . )

The alternative distal head configuration 30b shown in FIGS. 5–7 provides a distal head member 30b having a frontal portion 36b and a rear portion 38b. Said frontal portion 36b having an outer diameter substantially equal to the outer diameter of the adjacent catheter body 18. Said rear portion 38b has an outer diameter substantially equal to the inner diameter of the distal end of the catheter lumen 26. By such configuration, the rear portion 38b of the distal head member 30b may be inserted into the distal end of the catheter lumen 26b and secured thereto by frictional engagement, mechanical engagement, heat sealing, chemical adhesive, or any other suitable means. When so constructed, the lateral outer surface of the distal head member 30b is continuous, and substantially flush with the adjacent outer surface of the catheter body 18, as shown. The alternative distal head member 30b shown in FIGS. 5–7 also differs from the distal head member 30a shown in FIGS. 2–4 in that the guidewire passageway 40b serves as the central fluid passageway of the distal head 30b, as well as serving as the guidewire passageway through which a guidewire may pass longitudinally through the distal head member 30b (see guidewire shown in phantom lines).

Fluid outflow passageways 42b pass fluid laterally outward from the central guidewire lumen fluid passageway 40b and lead to multiple fluid outflow apertures 34b. Thus, when the guidewire (phantom lines) has been removed or retracted so as not to block fluid entry into the guidewire passage lumen/central fluid passageway 40b, irrigation/dilation/coolant fluid may be infused through the lumen 26b of the catheter body 18, through the guidewire passageway/central fluid passageway 40b and subsequently outward through the lateral fluid passageways 42b and lateral fluid outflow apertures 34b, as well as through the frontal guidewire passageway opening 40b. The flow rate and volume of fluid so infused may be controlled to effect any desired degree of irrigation or dilation of a surrounding anatomical structure (e.g., fallopian tube, ureter, blood vessel or other anatomical passageway).

ii. Preferred Modes of Operation of the First Embodiment

The ultrasound system 10 of the first embodiment shown in FIGS. 1–7 may be utilized for ultrasonic treatment of various obstructive disorders of the mammalian body wherein it is desirable to effect concomitant fluid irrigation or fluid dilation of the anatomical structure whereat the distal end of the catheter 18 is positioned.

Examples of procedures wherein the ultrasound system 10 of the first embodiment may be employed include the ultrasonic ablation of atherosclerotic plaque, thrombus or other obstructive matter within the lumen(s) of mammalian blood vessel(s). Also, as described more fully in the examples set forth herebelow, the ultrasound system 10 of the first embodiment may be utilized to effect dilation and/or removal of obstructive matter (e.g., scar tissue, tumors, congenitally aberrant tissue, etc. . . . ) which obstruct tubular passageways of the body including the ducts and passageway of the urogenital tract (e.g., urethra, ureter, fallopian tubes).

EXAMPLE 1

In a first example, an ultrasound system 10 of the first embodiment of the present invention may be utilized to treat obstructions of the fallopian tubes of a female human being.

Fallopian tube obstructions are known to occur due to the formation of scar tissue within the lumens of the fallopian tubes following the occurrence of fallopian tube infections, such as chlamydia infections.

In treating such blockage of the fallopian tubes, a standard guidewire having an outer diameter of approximately 0.14÷0.25 inch is inserted transvaginally and advanced, with radiographic and/or endoscopic guidance, into the obstructed fallopian tube to a point where the distal end of the guidewire 50 is situated adjacent the offending fallopian tube obstruction. After the guidewire has been positioned, the proximal end of the guidewire 50 is inserted into the distal guidewire passageway 40 of the catheter 18 and the catheter 18 is advanced over the guidewire, using standard catheter advancement technique, to a point where the distal head 30 of the catheter 18 has been advanced to a position adjacent the obstruction to be treated. During such advancement of the catheter, the proximal end of the guidewire 50 will emerge out of the guidewire sidearm 52 of the proximal connector assembly 22 so as to render the proximal portion of the guidewire freely accessible to the operator for subsequent manipulation, extraction or exchange of the guidewire 50, if desired.

The pressurized fluid source or pump 28 is then utilized to pass a flow of irrigation/dilation fluid, such as 0.9% NaCl solution or other physiologically compatible liquid, through line 56 and into sidearm 24 of proximal end connector assembly 22. The fluid so infused will then pass, in the distal direction, through the internal bore of the proximal connector assembly 22, through the lumen 26 of catheter 18 and out of the fluid outflow apertures 34 of the distal head 30 of the catheter device 16.

The flow rate of irrigation/dilation fluid out of outflow apertures 34 may be adjusted and controlled so as to provide a controlled degree of a) fluid-induced dilation of the fallopian tube lumen immediately adjacent the obstruction to be treated and/or b) impingement of fluid against the obstructing scar tissue or other matter.

Thereafter, the signal generator 12 may be energized by depression of on/off foot pedal 11, thereby sending an electrical signal through line 13 to ultrasound transducer 14. Such electrical signal is converted to ultrasonic vibration by ultrasound transducer 14 and the ultrasonic vibration is passed, via proximal connector assembly 22, into the ultrasound transmission wire or member 20, thereby causing ultrasonic vibration of the distal head 30 of the catheter 16.

With continued infusion of the irrigation/dilation fluid, the catheter 16 may be advanced, or otherwise moved back and forth, such that the ultrasonic vibration of the distal head 30 of the catheter 16 will effect morcellation or reduction of the obstructive matter. Such morcellation or reduction of the obstructive matter by the ultrasonic vibration of the distal head 30 may be effected by direct contact of the vibrating distal head 30 against the obstructive matter and/or by cavitation effect created as a result of the ultrasonically vibrating distal head 30 in the fluid environment created by the controlled infusion of the infusion/dilation fluid adjacent the obstructive lesion to be treated.

In some cases it may be desirable to initially employ a first catheter 16 having a distal head 30 designed for initial dilation of the surrounding fallopian tube lumen and impingement of the irrigation fluid against the offending lesion, and to subsequently utilize one or more additional embodiments of the catheter 16 having different designs of the distal head 30 so as to effect differing degrees of fluid impingement against the offending lesion and/or fluidic dilation of the surrounding luminal wall of the fallopian tube, during differing stages of the procedure. For example, in some procedures it may be desirable to utilize three(3) separate catheter devices 16, as follows:

| CATHETER 1 | Small size (OD = .5–1.2 mm) | Distal head having one or more fluid outflow apertures in frontal surface of tip to direct irrigation/dilation fluid into direct impingement with obstructive matter. |
|---|---|---|
| CATHETER 2 | Medium size (OD = 1.2–2.0 mm) | Distal head having fluid outflow apertures in frontal surface of tip and around the lateral sides of tip so as to simultaneously direct irrigation/dilation fluid in a) a forward direction so as to impinge against the obstructive matter and b) in lateral directions so as to exert external dilatory pressure against the surrounding tube wall. |

-continued

| CATHETER 3 | Large size (OD = 2.0–3.5 mm) | Distal head having no fluid outflow apertures in front surface of tip and multiple fluid outflow apertures around lateral sides of tip to exert lateral dilatory pressure against the surrounding tube only. |
|---|---|---|

In addition to effecting ultrasonic ablation or breakdown of the obstructive matter, the ultrasonic vibration of the distal head 30 of the catheter 16 may also cause relaxation of smooth muscle and resultant dilation of the fallopian tube, thereby permitting the catheter 16 to be advanced back and forth through the previously obstructed region of the fallopian tube.

In this example, it is preferable that the ultrasonic vibration of the distal catheter tip 30 be of an optimized frequency and wave form modulation to effect the desired ablation of the obstruction for inducing smooth muscle relaxation and resultant dilation of the obstructed fallopian tube.

One or more inflatable dilation balloons mounted on the ultrasound catheter device 16 or mounted on a separate balloon catheter may be utilized in conjunction with the ultrasound catheter 16, to effect dilation and opening of the obstructed region of the fallopian tube.

After the procedure has been completed and the patency of the obstructed fallopian tube restored, the catheter 16 may be extracted and removed.

EXAMPLE 2

In a second example, the ultrasound system 10 of the first embodiment of the present invention may be utilized to treat obstructions of the male urethra resulting from benign prostatic hypertrophy or other prostate enlargement.

In this example, the catheter device 16 of the first embodiment is inserted, with or without the assistance of a pre-inserted guidewire 50, into the male urethra. The catheter 16 is then advanced to a point where the distal head 30 of the catheter 16 is positioned adjacent the obstructing prostatic tissue.

A pressurized fluid source or pump 28 may be utilized to pump or otherwise expel fluid through tube 54, through sidearm 24, through the longitudinal bore of the proximal connector assembly 22, through the lumen 26 of catheter 16 and out of the distal fluid outflow apertures 34. The flow rate and quantity of the irrigation/dilation fluid being infused may be specifically adjusted and/or controlled so as to effect the desired degrees of a) impingement of the fluid against the obstruction and/or b) fluidic dilation of the surrounding anatomical structures (e.g., the urethra).

Concomitant with the infusion of the irrigation/dilation fluid, signal generator 12 may be energized by depression of on/off foot pedal 11, thereby sending an electrical signal through line 13 to ultrasound transducer 14. Ultrasound transducer 14 will convert the electrical signal to ultrasonic vibration and, via proximal connector assembly 22, will pass such ultrasound vibration through ultrasound transmission member 20 to the distal head 30 of the catheter 16. Ultrasonic vibration from the catheter tip may thereby result in a) relaxation and dilation of the smooth muscle of the urethra and/or b) ultrasonic ablation or morselling of the obstruction.

For smooth muscle relaxation the preferred ultrasound frequency is 20 kz to 1 MHz. For morselling or ablating the obstructing prostate tissue, the preferred ultrasound frequency is 20 kz to 100 MHz.

As described above in Example 1, it may also be desirable to utilize two or more separate catheters 16 having distal heads 30 of differing design, with different positions and configurations of the fluid outflow apertures 34, to facilitate optimal performance of various phases of the procedure.

After the prostatic obstruction of the urethra has been ultrasonically ablated and/or dilated so as to restore patency and urinary flow through the urethra, the catheter 16 may be extracted and removed.

The foregoing Examples 1 and 2 are intended to illustrate certain specific intended applications of the ultrasound system 10 of the first embodiment of the invention, and are not intended to provide a comprehensive discussion of all possible ablative or dilative procedures wherein the ultrasound system 10 may be employed iii. Elements and Components of the Second Embodiment FIGS. 8–11 of the drawings are directed to a second embodiment of an ultrasound system 10a of the present invention. As shown, such second embodiment ultrasound system 10a generally comprises a signal generator 12a, an ultrasound transducer 14a and an elongate catheter 16a, having a proximal connector assembly 22a positioned on the proximal end thereof for coupling the catheter 16a to the ultrasound transducer 14a.

The proximal connector assembly 22a of the second embodiment ultrasound system 10a may be constructed and configured substantially the same as that described hereabove and in incorporated U.S. Pat. No. 5,267,954 (Nita), however it will be appreciated that in accordance with the showing of the second embodiment in FIG. 8 of this patent application such ultrasound connector assembly 22a will include an additional suction or aspiration sidearm 60 and a separate suction or aspiration tube or secondary lumen (not shown) within the hollow bore of the connector assembly 22a and which is continuous with and fluidically connected to an aspiration lumen or tube member to which extends longitudinally through the catheter body 18a for withdrawal or aspiration of debris.

The catheter 16a preferably comprises an elongate flexible catheter sheath having an ultrasound transmission member or wire 20a extending longitudinally therethrough. The proximal end of the ultrasound transmission member or wire 20a extends proximally through the proximal connector assembly 22a and is thereby coupleable or connectable to the ultrasound transducer 14a. The distal end of the ultrasound transmission member wire 20a is coupled or connected to the distal head member 30a of the catheter 16a so as to transmit ultrasonic vibration into the distal head member 30a.

The catheter 16a of the second embodiment shown in FIGS. 8–11 is a "monorail" type of catheter having a guidewire passage lumen 51 extending only through a distal portion of the catheter body 18a. In the embodiment shown, the guidewire passage lumen 51 comprises a tube which extends from the distal guidewire passage aperture 40a formed in the distal end of the distal head member 30a to a sidewall guidewire passage aperture 41a formed in the sidewall of the catheter body 18a, at a location such as that shown in FIG. 8. By such "monorail" arrangement, the proximal end of a guidewire may be passed into distal guidewire aperture 40c and advanced through guidewire lumen 51 so as to subsequently exit the catheter body 18a through sidewall aperture 41a. The proximal portion of the guidewire 50 may reside outboard of the catheter body 18a as is typical of "monorail" type catheters.

It will be appreciated that an over-the-wire embodiment may also be designed incorporating a guidewire tube or lumen which extends longitudinally through the entire catheter body 18a, with a separate guidewire passage sidearm formed in the proximal connector 22a, in a manner similar or the same as that shown in FIG. 1 with respect to the first embodiment described hereabove.

An aspiration tube member 70 extends longitudinally through the internal bore 26a of the catheter body 18a and longitudinally through a separate dedicated bore formed in the distal head member 30a as shown. The distal end of the aspiration tube member 70 is flush with the distal or frontal face of the distal head member 30a. The proximal end of the aspiration tube member 70 is fluidly connected or continuous with aspiration sidearm 60, thereby forming a continuous dedicated aspiration channel through the catheter 16a. Aspiration pump 62 is connected to aspiration sidearm 60 by way of tube 64. Debris collection vessel 66 is connected to aspiration pump 62 by tube 68. By such arrangement, aspiration pump 62 may be utilized to withdraw or aspirate debris from the area adjacent the distal end of the catheter, in a proximal direction, through aspiration tube member 70 and into debris collection vessel 66.

iv. Preferred Modes of Operation of the Second Embodiment

With reference to FIGS. 8–11, the ultrasound system 10a of the second embodiment may be operated to effect ultrasonic dilation, morselling, pulverization or other treatment of obstructive matter within a vessel or passageway of a mammalian body. Concomitant with or separate from the ultrasonic treatment, the system 10a may also be utilized to a) infuse irrigation/coolant/dilation fluid through the catheter 16a and out of the distal end thereof and b) aspirate debris, fluid or other matter, in a proximal direction, through the catheter 16a and into the debris collection vessel 66.

The aspiration and debris collection capability of the system 10a of the second embodiment is particularly useful in applications wherein it is desired to promptly remove or suction away any particles of solid matter which may be created or liberated as a result of the ultrasonic treatment process. The ability to aspirate and suction away debris or particles of solid matter is particularly important in vascular applications, wherein it is desirable to avoid any embolization or migration of solid matter into the organ or tissue, which is perfused by the blood vessel wherein the treatment is being applied. For example, in procedures wherein ultrasound is utilized to treat or ablate obstructions of the extracranial and/or intracranial blood vessels which profuse the brain, it is highly desirable to prevent the passage of any solid particulate matter into the brain, as such may result in highly undesirable sequelae such as introgenic stroke or embolization of smaller blood vessels which may be situated downstream from the site of the treatment procedure. In such cerebrovascular applications, the ability to promptly aspirate any solid particles which may have been created or released by the ultrasonic procedure is useful to prevent such solid particles from resulting in untoward embolization of the brain.

Arterial blood flow to the brain is provided mainly by four(4) large extracranial arteries, two common carotid arteries and two(2) vertebral arteries, which feed smaller intracranial arteries. The two(2) vertebral arteries originate from the right and left subclavian arteries, respectively, and pass into the cranium through the foramen magnum. The vertebral arteries give off branches to form the anterior spinal artery, the posterior and inferior cerebellar arteries, and the basilar artery. The common carotid arteries bifurcate into the internal and external carotid arteries. The internal carotid arteries pass into the cranium and give off the ophthalmic, posterior communicating and anterior choroidal arteries. The internal carotid arteries also form, by terminal bifurcation, the anterior and middle cerebral arteries.

Obstructions may form in any of the intracranial or extracranial cerebral arteries, including all of those described hereabove. Such obstructions may result from atherosclerotic narrowing of those arteries, or may come about due to a thromboembolic event, such as the migration of a blood clot into the cerebral circulation from the heart or some other location.

The clinical significance and severity of symptoms resulting from obstruction of the cerebral blood vessels may vary, depending on the origin or type of obstruction, the location of the obstruction and other factors. The degrees of resultant ischemia may vary, ranging from a) a "transient ischemic attack" (TIA) wherein a transient focal loss of neurologic function occurs, to b) a "partial non-progressing stroke" (PNS) producing minor persistent neurologic disability to c) a "completed stroke" (CS) producing major permanent neurologic disability.

The following are examples of applications wherein the ultrasound system 10a of the second embodiment of the present invention is utilized to treat obstructions of the cerebral blood vessels so as to treat or prevent conditions such as TIA, PNS or CS as described hereabove.

EXAMPLE 3

In this example, the second embodiment of the ultrasound system 10a shown in FIGS. 8–11 is utilized to treat an atherosclerotic obstruction of the extracranial internal carotid artery of a human being.

Initially, a guidewire 50 is percutaneously inserted into a peripheral artery and advanced, under radiologic guidance, to a position whereat the distal end of the guidewire 50 is positioned in the internal carotid artery immediately upstream of the obstruction to be treated.

The proximal end of the guidewire is passed into the distal guidewire aperture 40a of the catheter device 16a and the catheter device 16a is advanced over the guidewire, with the proximal end of the guidewire 50 emerging from the sidewall guidewire aperture 41a as the catheter 16a is further advanced to a point where the distal head 30a of the catheter 16a is positioned adjacent the obstruction to be treated.

The guidewire 50 is then fully or partially withdrawn into the tubular guidewire lumen 51 of the catheter device 16a.

Foot pedal 11a is depressed to energize signal generator 12a such that an electrical signal emitted by signal generator 12a passes through line 13a to ultrasound transducer 14a. Ultrasound from ultrasound transducer 14a passes, via proximal connector assembly 22a, into the proximal end of the ultrasound transmission member 20a and travels through ultrasound transmission member 20a to distal head member 30a, thereby causing ultrasonic vibration of distal head member 30a.

Concomitant with the delivery of ultrasound to the distal head member 30a, a flow of 0.9% NaCl solution is pumped via pump 28a, through the catheter lumen 26a. Such flow of saline solution through the catheter lumen 26a accomplishes the dual function of a) bathing and cooling the ultrasound transmission member 20a to prevent excessive heat build-up as a result of the ultrasonic vibration thereof and b) providing a flow of irrigation/dilation fluid into central fluid passageway 32a, through secondary fluid passageway 42a and out of fluid outflow apertures 34a.

Also, concomitant with the delivery of ultrasound to the distal head 30a and the infusion of irrigation/dilation fluid out of fluid outflow apertures 34a, a suction is applied, via suction pump 62, through line 64 to aspiration sidearm 60, thereby drawing negative pressure on the lumen of aspiration tube 70 so as to draw particulate matter or other debris adjacent the distal tip of the catheter 16a into the distal aspiration port 72, through aspiration tube 72 and into debris collection vessel 66.

The flow of saline solution out of the fluid outflow apertures 34a and the intake of matter into aspiration port 72 may be adjusted and controlled, by adjustment and control of infusion pump 28a and aspiration pump 62, such that the two(2) flow rates are substantially equal to one another, such that saline solution flowing out of the fluid outflow apertures 34a will circulate adjacent the distal head member and be subsequently withdrawn into the aspiration port 72a and through aspiration tube 70 into debris container 66. By such equilibration of the infusion outflow and aspiration outflow rate, a continuous fluid turnover may be affected to accomplish prompt lavage and removal of any particulate matter or other debris generated adjacent the distal head 30a of the catheter device 16a.

The catheter 16a may be proximally advanced and/or moved back and forth so as to effectively treat the obstructive lesion, thereby improving blood flow and restoring patency to the lumen of the internal carotid artery wherein the treatment is applied.

When desired, the aspiration pump 62 may be turned off and a quantity of radiographic contrast medium may be passed into infusion sidearm 58, through catheter lumen 26a and out of distal fluid outflow apertures 34a to radiographically visualize the area of the obstruction for purposes of determining whether the treatment has effectively ablated or opened the obstruction.

After successful treatment and opening of the obstruction has been radiographically verified, the catheter device 16a may be withdrawn and removed.

EXAMPLE 4

In this example, the second embodiment of the ultrasound system 10a shown in FIGS. 8–11 is utilized to ultrasonically treat an obstruction of the intracranial middle cerebral artery of a human being.

Initially, a guidewire 50 is percutaneously inserted into a peripheral artery and advanced, under radiographic guidance, to a position whereat the distal end of the guidewire 50 is positioned within the cerebral artery, immediately upflow of the obstruction to be treated.

Thereafter, the proximal end of the guidewire 50 is inserted into the guidewire entry aperture 40a in the distal head 30a of the catheter device 16a and the catheter device 16a is advanced in the proximal direction, with the proximal end of the guidewire 50 emerging outwardly through sidewall guidewire aperture 44a. The advancement of the catheter 16a is continued until the distal head 30a is positioned in the middle cerebral artery immediately adjacent the obstruction to be treated.

Thereafter, the guidewire 50 is fully or partially withdrawn, at least to a point whereat the distal tip of the guidewire is within the guidewire tube 51 internal of the body of catheter 16a.

Foot pedal 11a is depressed to energize signal generator 12a, thereby sending an electrical signal through line 13a to ultrasound transducer 14a. Ultrasound from transducer 14a passes, via proximal connector assembly 22a, into ultrasound transmission member 20a and is carried by said ultrasound transmission member 20a to the distal head 30a of the catheter device 16a, thereby causing the distal head 30a to vibrate ultrasonically within the desired frequency range.

Relaxation of the vascular smooth muscle within the middle cerebral artery results from the ultrasonic vibration within the above-stated frequency range, thereby causing some dilation of the middle cerebral artery in the region of the obstruction to be treated.

Concomitant with the delivery of ultrasound to the distal head member 30a, a flow of 0.9% NaCl solution is pumped via pump 28a, through the catheter lumen 26a. Such flow of saline solution through the catheter lumen 26a accomplishes the dual function of a) bathing and cooling the ultrasound transmission member 20a to prevent excessive heat build-up as a result of the ultrasonic vibration thereof and b) providing a flow of irrigation/dilation fluid into central fluid passageway 32, through secondary fluid passageway 42c and out of fluid outflow apertures 34c.

Also, concomitant with the delivery of ultrasound to the distal head 30a and the infusion of irrigation/dilation fluid out of fluid outflow apertures 34a, a suction is applied, via suction pump 62, through line 64 to aspiration sidearm 60, thereby drawing negative pressure on the lumen of aspiration tube 70a so as to draw particulate matter or other debris adjacent the distal tip of the catheter 16a into the distal aspiration port 72a, through aspiration tube 70a and into debris collection vessel 66.

The flow of saline solution out of the fluid outflow apertures 34a and the intake of matter into aspiration port 72 may be adjusted and controlled, by adjustment and control of infusion pump 28a and aspiration pump 62, such that the two(2) flow rates are substantially equal to one another, such that saline solution flowing out of the fluid outflow apertures 34a will circulate adjacent the distal head member and be subsequently withdrawn into the aspiration port 72a and through aspiration tube 70a into debris container 66. By such equilibration of the infusion outflow and aspiration outflow rate, a continuous fluid turnover may be affected to accomplish prompt lavage and removal of any particulate matter or other debris generated adjacent the distal head 30a of the catheter device 16a.

The catheter 16a may be proximally advanced and/or moved back and forth so as to effectively treat the obstructive lesion, thereby improving blood flow and restoring patency to the lumen of the internal carotid artery wherein the treatment is applied.

When desired, the aspiration pump 62 may be turned off and a quantity of radiographic contrast medium may be passed into infusion sidearm 58, through catheter lumen 26a and out of distal fluid outflow apertures 34a to radiographically visualize the area of the obstruction for purposes of determining whether the treatment has effectively ablated or opened the obstruction.

After successful treatment and opening of the obstruction has been radiographically verified, the catheter device 16a may be withdrawn and removed.

It will be appreciated that the foregoing drawings, descriptions of preferred embodiments, and examples serve to describe and illustrate specific embodiments of the invention but do not describe or encompass every possible embodiment of the invention which may be constructed or utilized. Accordingly, it is intended that the above-set-forth description, drawings and examples be broadly construed so as to encompass all foreseeable additions, modifications and alterations which those of skill in the art would be inclined to make.

What is claimed is:

1. An ultrasound catheter device for delivering ultrasound from an external ultrasound source to a location inside a mammalian body, said device comprising:

(a) a tubular catheter body having a proximal end, a distal end, at least one lumen extending longitudinally therethrough and a longitudinal axis;

(b) a distal head member comprising a plug at least partially inserted into the distal end of the lumen of the catheter body, said distal head member having a lateral sidewall and a frontal surface and a plurality of fluid passageways and fluid outflow apertures formed at spaced locations about the lateral surface of said distal head member to expel fluid in outward directions generally perpendicular to the longitudinal axis of said catheter body said fluid passageways being configured to carry fluid from said catheter lumen, through said fluid passageway and out of said fluid outflow apertures;

(c) a proximal connector assembly on the proximal end of said catheter body, said proximal connector assembly having at least one bore extending longitudinally therethrough in fluid connection with the lumen of said catheter body, and at least one fluid infusion port to permit infusion of fluid;

(d) an ultrasound transmission member having a proximal end and a distal end, said ultrasound transmission member extending longitudinally through the lumen of said catheter body and into the bore of said proximal connector assembly, the distal end of said ultrasound transmission member being in contact with said distal head member and the proximal end of said ultrasound transmission member being coupleable, by way of said proximal connector assembly, to said external ultrasound source;

(e) said catheter device being thereby constructed to concomitantly deliver;

(i) ultrasonic vibration from said ultrasound source to the distal head member of said catheter; and (ii) a flow of infusion/dilation fluid through said catheter body and out of said fluid outflow apertures.

2. An ultrasound catheter device for delivering ultrasound from an external ultrasound source to a location inside a mammalian body, said device comprising:

(a) a tubular catheter body having a proximal end, a distal end, at least one lumen extending longitudinally therethrough and a longitudinal axis;

(b) a distal head member comprising a plug at least partially inserted into the distal end of the lumen of the catheter body, said distal head member having a central fluid passageway extending longitudinally therein to and fluidly communicative with the lumen of said catheter, said central fluid passageway leading to a plurality of secondary fluid passageways which lead to a plurality of fluid outflow apertures, respectively, so as to carry infusion fluid from the lumen of said catheter, through said distal head member and out of said plurality of fluid outflow apertures;

(c) a proximal connector assembly on the proximal end of said catheter body, said proximal connector assembly having at least one bore extending longitudinally therethrough in fluid connection with the lumen of said catheter body, and at least one fluid infusion port to permit infusion of fluid;

(d) an ultrasound transmission member having a proximal end and a distal end, said ultrasound transmission member extending longitudinally through the lumen of said catheter body and into the bore of said proximal connector assembly, the distal end of said ultrasound transmission member being in contact with said distal head member and the proximal end of said ultrasound transmission member being coupleable, by way of said external connector assembly, to said proximal ultrasound source;

(e) said catheter device being thereby constructed to concomitantly deliver;

(i) ultrasonic vibration from said ultrasound source to the distal head member of said catheter; and (ii) a flow of infusion/dilation fluid through said catheter body and out of said fluid outflow apertures.

* * * * *

UNITED STATES PATENT AND TRADEMARK OFFICE
CERTIFICATE OF CORRECTION

PATENT NO. : 5,957,882
DATED : Sep. 28, 1999
INVENTOR(S) : Henry Nita, Timothy C. Mills It is certified that error appears in the above-identified patent and that said Letters Patent is hereby corrected as shown below:

Column 4, line 8, change "34", to read --34a--.

Column 4, line 12, change "30", to read --30a--.

Column 4, line 18, change "30", to read --30a--.

Column 4, line 19, after "lumen", delete "26".

Column 4, line 29, change "30", to read --30a--.

Column 4, line 30, change "32", to read --32a--.

Column 4, line 33, change "30", to read --30a--.

Column 4, line 35, change "32", to read --32a--.

Column 4, line 35, change "30", to read --30a--.

Column 4, line 37, change "42", to read --42a--.

Column 4, line 37, change "34", to read --34a--.

Column 4, line 39, change "40", to read --40a--.

Column 4, line 41, change "40", to read --40a--.

Column 8, line 49, change "30a", to read --30c--.

Column 8, line 51, change "30a", to read --30c--.

Column 8, line 57, change "40a", to read --40c--.

UNITED STATES PATENT AND TRADEMARK OFFICE
CERTIFICATE OF CORRECTION

PATENT NO. : 5,957,882
DATED : Sep. 28, 1999
INVENTOR(S) : Henry Nita, Timothy C. Mills It is certified that error appears in the above-identified patent and that said Letters Patent is hereby corrected as shown below:

Column 8, line 58, change "30a", to read --30c--.

Column 9, line 11, change "30a", to read --30c--.

Column 9, line 13, change "30a", to read --30c--

Column 10, line 47, change "30a", to read --30c--.

Column 10, line 58, change "30a", to read --30c--.

Column 10, line 59, change "30a", to read --30c--.

Column 10, line 61, change "30a", to read --30c--.

Column 11, line 1, change "32a", to read --32c--.

Column 11, line 2, change "34a", to read --34c--.

Column 11, line 4, change "30a", to read --30c--.

Column 11, line 5, change "34a", to read --34c--.

Column 11, line 10, after "port", delete "72".

Column 11, line 10, change "72", to read --70--.

Column 11, line 13, change "34a", to read --34c--.

Column 11, line 13, after "port", delete "72".

Column 11, line 18, change "34a", to read --34c--.

UNITED STATES PATENT AND TRADEMARK OFFICE
CERTIFICATE OF CORRECTION

PATENT NO. : 5,957,882
DATED : Sep. 28, 1999
INVENTOR(S) : Henry Nita, Timothy C. Mills Page 3 of 4

It is certified that error appears in the above-identified patent and that said Letters Patent is hereby corrected as shown below:

Column 11, line 19, after "port", delete "72a".

Column 11, line 24, change "30a", to read --30c--.

Column 11, line 34, change "34a", to read --34c--.

Column 11, line 54, change "40a", to read --40c--.

Column 11, line 55, change "30a", to read --30c--.

Column 11, line 58, after "aperture", delete "44a".

Column 11, line 59, change "30a", to read --30c--.

Column 12, line 4, change "30a", to read --30c--.

Column 12, line 6, change "30a", to read --30c--.

Column 12, line 14, change "30a", to read --30c--.

Column 12, line 21, change "32", to read --32c--.

Column 12, line 24, change "30a", to read --30c--.

Column 12, line 25, change "34a", to read --34c--.

Column 12, line 28, change "70a", to read --70--.

Column 12, line 30, after "port", delete "72a"

Column 12, line 30, change "70a", to read --70--.

UNITED STATES PATENT AND TRADEMARK OFFICE
CERTIFICATE OF CORRECTION

PATENT NO. : 5,957,882
DATED : Sep. 28, 1999
INVENTOR(S) : Henry Nita, Timothy C. Mills It is certified that error appears in the above-identified patent and that said Letters Patent is hereby corrected as shown below:

Column 12, line 33, change "34a", to read --34c--.

Column 12, line 33, after "port", delete "72".

Column 12, line 38, change "34a", to read --34c--.

Column 12, line 39, after "port", delete "72a".

Column 12, line 44, change "30a", to read --30c--.

Column 12, line 55, change "34a", to read --34c--.

Signed and Sealed this

Twenty-third Day of May, 2000

Attest:

Q. TODD DICKINSON

*Attesting Officer*     *Director of Patents and Trademarks*